(12) United States Patent
Ganzoni

(10) Patent No.: US 11,273,080 B2
(45) Date of Patent: Mar. 15, 2022

(54) COMPRESSION GARMENT FOR ONE-HAND OPERATION

(71) Applicant: SIGVARIS AG, St. Gallen (CH)

(72) Inventor: Levin Andreas Ganzoni, Zurich (CH)

(73) Assignee: SIGVARIS AG, St. Gallen (CH)

( * ) Notice: Subject to any disclaimer, the term of this patent is extended or adjusted under 35 U.S.C. 154(b) by 290 days.

(21) Appl. No.: 16/332,355

(22) PCT Filed: Sep. 5, 2017

(86) PCT No.: PCT/EP2017/072211
§ 371 (c)(1),
(2) Date: Mar. 12, 2019

(87) PCT Pub. No.: WO2018/054681
PCT Pub. Date: Mar. 29, 2018

(65) Prior Publication Data
US 2019/0209387 A1    Jul. 11, 2019

(30) Foreign Application Priority Data

Sep. 20, 2016   (CH) .................... 01222/16

(51) Int. Cl.
*A61F 13/08* (2006.01)
*A61F 5/01* (2006.01)
*A61F 5/32* (2006.01)

(52) U.S. Cl.
CPC .............. *A61F 13/085* (2013.01); *A61F 5/01* (2013.01); *A61F 5/0104* (2013.01); *A61F 5/32* (2013.01); *A61F 13/08* (2013.01)

(58) Field of Classification Search
CPC .......... A61F 13/085; A61F 13/08; A61F 5/01; A61F 5/0104; A61F 5/32;
(Continued)

(56) References Cited

U.S. PATENT DOCUMENTS 2,687,723 A   8/1954   Stern
3,613,679 A   10/1971  Bijou
(Continued)

FOREIGN PATENT DOCUMENTS

AU        6414174 A       7/1975
AU        2017329457 A1   2/2019
(Continued)

OTHER PUBLICATIONS

CircAid JuxtaFit Essentials arm sleeve by Medi; http://mediusa.com/portfolio-item/juxtafit-essentials-upper-extremity/; Mar. 29, 2015.
(Continued)

*Primary Examiner* — Tarla R Patel
(74) *Attorney, Agent, or Firm* — Fisherbroyles, LLP; Anthony J DoVale

(57) ABSTRACT

A compression garment comprises an elongated stretchable sleeve (1) which is adapted to be worn over a body part and a compression part (2) connected to the elongated stretchable sleeve (1). The garment has at least one closing part (3) for fixing the compression part (2) in a stretched state. Furthermore, the compression part (2) is shaped and sized to be wrapped around the circumference of the elongated stretchable sleeve (1), wherein the compression part (2) is adapted for positioning proximate to an outer surface of the elongated stretchable sleeve (1).

10 Claims, 3 Drawing Sheets

(58) Field of Classification Search
CPC .......... A61F 13/00038; A61F 13/00085; A61F 5/0109; A61F 7/02; A61F 13/107; A61F 2013/15317; A61F 2013/15325; A61F 2250/0018; A61F 2002/30014; A61F 13/102

See application file for complete search history.

(56) References Cited

U.S. PATENT DOCUMENTS

| | | | |
|---|---|---|---|
| 3,856,008 A | 12/1974 | Fowler et al. | |
| D234,271 S | 2/1975 | Moore | |
| 4,215,687 A | 8/1980 | Shaw | |
| 4,367,733 A | 1/1983 | Stromgren | |
| D269,816 S | 7/1983 | Meier et al. | |
| 4,476,857 A | 10/1984 | Levine | |
| 5,108,455 A | 4/1992 | Telikicherla | |
| 5,254,122 A | 10/1993 | Shaw | |
| D353,005 S | 11/1994 | Glidden | |
| D382,344 S | 8/1997 | Swedberg et al. | |
| 5,904,145 A | 5/1999 | Reid | |
| 5,906,206 A | 5/1999 | Shaw et al. | |
| 6,152,893 A | 11/2000 | Pigg et al. | |
| 6,196,231 B1 | 3/2001 | Reid | |
| 6,254,554 B1 | 7/2001 | Turtzo | |
| 6,338,723 B1 | 1/2002 | Carpenter et al. | |
| 6,516,804 B1 | 2/2003 | Hoffman | |
| 7,329,232 B2 | 2/2008 | Lipshaw et al. | |
| 8,801,645 B2 | 8/2014 | Lipshaw et al. | |
| D717,453 S | 11/2014 | Mahtani | |
| D728,804 S | 5/2015 | Hansen | |
| 9,364,701 B2 | 6/2016 | Bartsch | |
| 9,642,559 B2 | 5/2017 | Falconio-West et al. | |
| 9,642,766 B2 | 5/2017 | Lipshaw et al. | |
| D800,325 S | 10/2017 | Cox | |
| D848,625 S | 5/2019 | Chase et al. | |
| D850,632 S | 6/2019 | Chiang et al. | |
| D872,286 S | 1/2020 | Hoffman et al. | |
| 2002/0062096 A1 | 5/2002 | Bennett | |
| 2005/0113729 A1* | 5/2005 | Scott ................ | A61F 13/085 602/19 |
| 2005/0148917 A1 | 7/2005 | Nathanson | |
| 2005/0192524 A1 | 9/2005 | Lipshaw et al. | |
| 2006/0201032 A1 | 9/2006 | Ramsey | |
| 2007/0179421 A1* | 8/2007 | Farrow .............. | A61H 1/008 602/75 |
| 2010/0269240 A1 | 10/2010 | Weir et al. | |
| 2010/0312160 A1 | 12/2010 | Creighton et al. | |
| 2011/0125183 A1 | 5/2011 | Lipshaw et al. | |
| 2011/0185508 A1 | 8/2011 | Hsu et al. | |
| 2011/0257575 A1* | 10/2011 | Farrow .............. | A61F 13/08 602/75 |
| 2012/0179084 A1 | 7/2012 | Lipshaw et al. | |
| 2012/0277073 A1 | 11/2012 | Bartsch | |
| 2013/0283500 A1 | 10/2013 | Lipshaw et al. | |
| 2013/0319128 A1 | 12/2013 | Richardson et al. | |
| 2015/0025424 A1 | 1/2015 | Richardson et al. | |
| 2015/0351969 A1* | 12/2015 | Farrow ............ | A61F 13/00059 601/150 |
| 2016/0000612 A1 | 1/2016 | Cox | |
| 2016/0030251 A1 | 2/2016 | Schuren et al. | |
| 2016/0030267 A1 | 2/2016 | Lipshaw et al. | |
| 2016/0100988 A1 | 4/2016 | Vee et al. | |
| 2016/0166458 A9 | 6/2016 | Lipshaw et al. | |
| 2017/0258672 A1 | 9/2017 | Wennen et al. | |
| 2018/0243143 A1 | 8/2018 | Karadsheh | |
| 2018/0344532 A1 | 12/2018 | Karadsheh et al. | |
| 2019/0133229 A1 | 5/2019 | Hoffman et al. | |
| 2019/0216653 A1 | 7/2019 | Ganzoni | |

FOREIGN PATENT DOCUMENTS

| | | |
|---|---|---|
| AU | 2017329458 A1 | 2/2019 |
| AU | 2018223706 A1 | 8/2019 |
| BR | 112019002388 A2 | 6/2019 |
| BR | 112019002399 A2 | 6/2019 |
| CA | 2 722 146 A1 | 10/2009 |
| CA | 3 037 413 A1 | 3/2018 |
| CA | 3 037 417 A1 | 3/2018 |
| CA | 3 054 339 A1 | 8/2018 |
| CH | 712 938 A1 | 3/2018 |
| CH | 712 939 A1 | 3/2018 |
| EP | 1052319 A1 | 11/2000 |
| EP | 1 959 880 A1 | 8/2008 |
| EP | 3 512 478 A1 | 7/2019 |
| EP | 3 512 479 A1 | 7/2019 |
| EP | 3 565 515 A1 | 11/2019 |
| FR | 2961389 | 12/2011 |
| MX | 2019001588 A | 9/2019 |
| MX | 2019001642 A | 9/2019 |
| MX | 2019009113 A | 9/2019 |
| WO | 95/16416 A1 | 6/1995 |
| WO | 99/30607 A2 | 6/1999 |
| WO | 00/15139 A2 | 3/2000 |
| WO | 01/89410 A2 | 11/2001 |
| WO | 2005/052235 A1 | 6/2005 |
| WO | 2013/085445 A1 | 6/2013 |
| WO | 2013/138394 A1 | 9/2013 |
| WO | 2014/116497 A1 | 7/2014 |
| WO | 2014160572 A1 | 10/2014 |
| WO | 2015188158 A2 | 12/2015 |
| WO | 2016/048827 A1 | 3/2016 |
| WO | 2016/105213 A1 | 6/2016 |
| WO | 2018/054681 A1 | 3/2018 |
| WO | 2018/054682 A1 | 3/2018 |
| WO | 2018/153611 A1 | 8/2018 |
| WO | 2019/091811 A1 | 5/2019 |

OTHER PUBLICATIONS

CircAid Arm Reduction Kit by Medi; http://mediusa.com/portfolio-item/circaid-reduction-kit/; May 20, 2016.
Solaris ReadyWrap arm sleeve by Lohmann & Rauscher; http://www.lymphedemaproducts.com/products/readywrap-arm.html; May 4, 2017.
Solaris TributeWrap Wrist to Axilla; https://www.lohmann-rauscher.com/us-en/products/solaris-collection-by-lr/tributewrap/; date unknown, at least prior to applicant's filing date of Feb. 1, 2018.
FarrowWrap LITE OTS Armpiece by Jobst; http://www.jobst-usa.com/product/jobst-farrow-ots-armsleeve/; Jul. 14, 2017.
FarrowWrap LITE Trim-To-Fit Armpiece by Jobst; http://www.jobst-usa.com/product/jobst-farrowwrap-lite-armpiece/; Jul. 14, 2017.
FarrowWrap Classic Custom Armpiece by Jobst; http://www.jobst-USA.com/product/jobst-farrowwrap-classic-armpiece/; Jul. 18, 2018.
Juzo Arm Compression Wrap; http://www.juzousa.com/Products/Product-Detail?ID=70; date unknown, at least prior to applicant's filing date of Feb. 1, 2018.
MedAssist ArmAssist by SIGVARIS; http://www.lymphedemaproducts.com/products/medassist-armassist.html; at least as of Oct. 17, 2017.
MedaFit Arm by SIGVARIS; https://www.sigvaris.com/usa/en-us/product/medafit; at least as of Jun. 10, 2017.
CompreSleeve Arm by SIGVARIS; https://www.sigvaris.com/usa/en-us/product/compresleeve; at least as of Jun. 10, 2017.
Notice of Allowance received for U.S. Appl. No. 29/635,709 dated Sep. 5, 2019, 18 pages.
International Search Report for International Application No. PCT/EP2018/051917 dated Mar. 12, 2018.
Non-Final Office Action received for U.S. Appl. No. 15/443,308 dated May 31, 2019, 28 pages.
Non-Final Office Action received for U.S. Appl. No. 15/443,308 dated Nov. 18, 2019, 17 pages.
Non-Final Office Action received for U.S. Appl. No. 15/808,092 dated Jan. 10, 2020, 32 pages.
International Search Report and Written Opinion received for PCT Application Serial No. PCT/US2019/045792 dated Oct. 28, 2019, 8 pages.
International Preliminary Report on Patentability received for PCT Application Serial No. PCT/EP2018/051917 dated Jun. 5, 2019, 10 pages.

(56) References Cited

OTHER PUBLICATIONS

International Search Report and Written Opinion received for PCT Application Serial No. PCT/EP2018/079569 dated Feb. 4, 2019, 8 pages.
International Search Report and Written Opinion issued in corresponding International Application No. PCT/EP2017/072213 dated Nov. 10, 2017.
International Preliminary Report on Patentability received for PCT Application Serial No. PCT/EP2017/072213 dated Apr. 4, 2019, 8 pages.
International Preliminary Report on Patentability received for PCT Application Serial No. PCT/EP2017/072211 dated Apr. 4, 2019, 16 pages.
International Search Report and Written Opinion issued in corresponding International Application PCT/EP2017/072211 dated Feb. 1, 2018.

\* cited by examiner

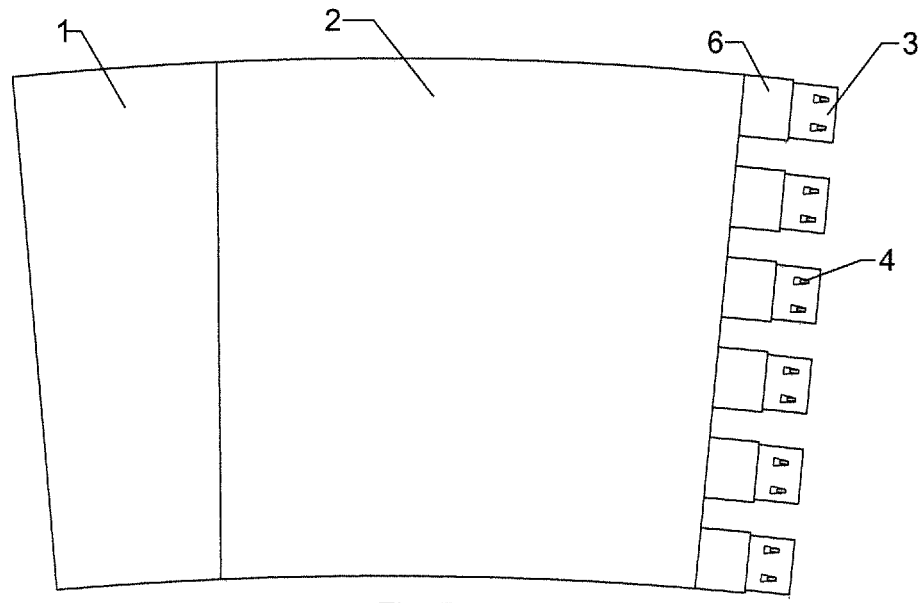
Fig. 5
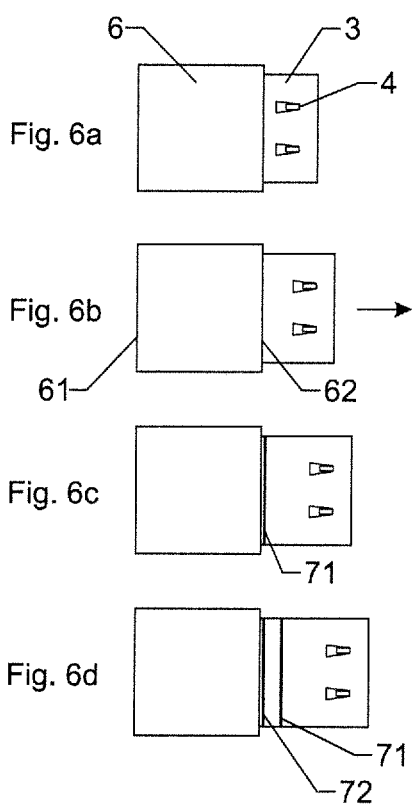
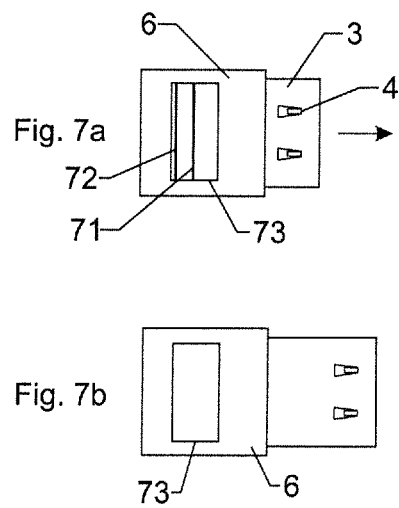

COMPRESSION GARMENT FOR ONE-HAND OPERATION

CROSS REFERENCES TO RELATED APPLICATIONS

This application claims the priority of Swiss patent application 01222/16, filed Sep. 20, 2016, the disclosure of which is incorporated herein by reference in its entirety.

TECHNICAL FIELD

The present invention relates to a compression garment, in particular stockings or a bandage, for applying compression to a body part.

BACKGROUND ART

Compression garments are used to provide a pressure or a compressive force, respectively, to a human body part, especially to a limb such as an arm or a leg for e.g. the treatment of venous diseases and lymphatic disorders. Medical compression garments are elastic or inelastic garments and can, for example, be used to compress a lower leg, an entire leg, an arm, a hand and so on. They are known to be designed as stockings, socks, panties, arm sleeves, gloves etc.

Many patients do not wear their compression garments due to difficulties in donning the garment and in dosing the compression force. Donning a compression garment over the lower leg is especially laborious. The torso has to be bent strongly forward if both hands are used at the same time for donning the compression garment.

DISCLOSURE OF THE INVENTION

The object of the present invention is to provide a compression garment which is easy to don.

In order to meet this object, a first aspect of the invention introduces a compression garment according to claim 1.

The compression garment comprises an elongated stretchable sleeve, a compression part and a closing part.

The elongated stretchable sleeve might be stretchable in both circumferential and longitudinal directions. The elongated stretchable sleeve has an inner surface and an outer surface and the sleeve is adapted to be worn over the body part to be compressed. The compression part is connected to the elongated stretchable sleeve and the at least one closing part is provided for fixing the compression part in a wrapped around state in which the body part is compressed by said compressing part.

The compression part is shaped and sized to be wrapped around at least a portion of the circumference of the elongated stretchable sleeve and the compression part is adapted for positioning proximate to the outer surface of the elongated stretchable sleeve. The compression part provides a compression force to the body part and is fixable by the closing parts in the wrapped around state to maintain the compression force.

This design allows an easy donning of the compression garment. While the compression part has the main function to generate the compression force, the elongated stretchable sleeve is primarily acting as a donning aid.

In a first step, the elongated stretchable sleeve can easily be pulled over the leg to bring the compression garment into position at the body part to be compressed. In a second step, the compression part, which is connected to the elongated stretchable sleeve, can be wrapped around the stretchable sleeve and thus around the body part by pulling on the compression part or pulling on the closing part connected to the compression part with one hand only. Then the compression part can be fixed by the closing part in the wrapped around state to secure the compression part in its wrapped around state providing the compression force to the body part.

The main advantage of the disclosed compression garment is that it can easily be donned only by one hand. The elongated stretchable sleeve stays steady in its position relative to the body part and does not rotate during wrapping around of the compression part even if considerable pulling force is exerted, since the compression part, when wrapped around the elongated stretchable sleeve, presses the elongated stretchable sleeve onto the body part and a rotating movement of the elongated stretchable sleeve is thus avoided due to friction. Therefore, while donning the compression garment, the compression part is held by the elongated stretchable sleeve on one side and is pulled by hand on the other side, either by pulling on the compression part or on the closing part. Thus it is not necessary that one part of the compression garment has to be held by one hand while the compression part is wrapped around and fixed by the other hand as in conventional devices.

In an advantageous embodiment, the compression part extends as a continuous part over the full length of the stretchable sleeve. In other words, the compression part is not designed as a plurality of tensile stripes, which generate local compression, but a continuous compression part is provided, which extends over the full length of the sleeve. A continuous compression part generates its compression force over the full body part to be compressed. In another advantageous embodiment, the compression part extends on one side even further than the length of the stretchable sleeve or the compression part extends on both sides further than the stretchable sleeve.

In an advantageous embodiment, the compression part extends over the full length of the body part to be compressed.

The extension over the full length of the body part allows an even pressure distribution over the full body part to be compressed.

In another advantageous embodiment, the compression part comprises a first end and the compression part is connected to the elongated stretchable sleeve by said first end only. A second end of the compression part is located opposite to the first end and the at least one closing part and preferably a plurality of closing parts are arranged adjacent to the second end. In another embodiment the edge of the elongated stretchable sleeve is sewn in with an offset from the edge of the compression part.

The first end and the second end have a functional meaning. If the compression part is wrapped around the stretchable sleeve, the force between the elongated stretchable sleeve and the compression part is transmitted over the first end of the compression part and the force between the compression part and the closing parts is transmitted over the second end of the compression part.

It is further preferred that the elongated stretchable sleeve is shaped and sized such that elongated stretchable sleeve alone applies an averaged pressure of less than approx. 15 mmHg (approx. 2000 Pa), in particular less than 10 mmHg (1333 Pa), in particular less than 5 mmHg (667 Pa), in particular less than 3 mmHg (400 Pa), to the body part.

The low pressure generated by the elongated stretchable sleeve allows an easy donning of the compression garment since the elongated stretchable sleeve can easily be pulled over the body part. Furthermore, a too high minimum pressure, which would act permanently on the body part by the elongated stretchable sleeve is avoided, but the pressure can individually be set to the preferred intensity by applying compression force by the compression part as much as wanted.

In another preferred embodiment, the elongated stretchable sleeve has a tubular form and/or is adapted to receive a leg or an arm.

In particular if the compression garment is designed to compress a leg, it can be donned more easily compared to conventional compression garments because only one hand is needed for donning it such that the torso does not have to be bent forward so much as with conventional garments. Donning is easier because the elongated stretchable sleeve goes easier over the heel as a medical compression stocking. The medial or lateral closure is easy to reach compared to garments with a closure over the shinbone area.

Advantageously, the elongated stretchable sleeve is integrally made of a material different than the material of the compression part or in the alternative the elongated stretchable sleeve is made in part of the material of the compression part and in part from a material different than the material of the compression part.

Preferably, the elongated stretchable sleeve shall not be thicker than 1 mm and have a stretchability of at least 100% in the preferred circumferential direction.

Furthermore, the compression part is preferably made of a spacer fabric.

In another advantageous embodiment, the compression part has an inner surface and an outer surface. Preferably, the at least one closing part and the outer surface of the compression part and of the elongated stretchable sleeve are adapted such that the at least one closing part can be attached to the outer surface of the compression part.

According to another aspect of the invention, a compression garment comprises a compression part, at least one closing part and at least one mark or gauge, respectively, applied to the at least one closing part for indicating when a proper amount of stretch has been reached by the closing part. The stretch of the closing part is an indication for the compression force applied by the compression part. The compression garment comprises at least one cover which at least partly covers the at least one closing part. The closing part is covered by the cover such that the at least one gauge is covered by the cover as long as a sufficient amount of stretch has not been reached and the at least one gauge is uncovered after a sufficient amount of stretch has been reached.

Alternatively the cover comprises a window such that the at least one gauge is covered by the cover if sufficient stretch has not been reached and is visible in the window if sufficient stretch has been reached, or is visible in the window if sufficient stretch has not been reached and is covered if sufficient stretch has been reached. A window can be an opening or a transparent cover, for example.

This embodiment has the advantage that the user realizes in a clear way when enough stretch has been reached within the closing part and thus indicating enough compression by the compression part while donning the compression garment. Enough stretch has been reached as soon as the gauge appears because it is not covered anymore or it disappears because it is covered after having been uncovered, depending on the design of the cover and the gauge.

The gauge can be designed as a simple line, or as any kind of figure.

More than one gauge can be applied to one closing part such that different levels of stretch can be indicated.

Furthermore, the at least one cover is preferably shaped as a bag. The at least one closing part is partly arranged inside the at least one bag such that the at least one closing part with the gauge can be pulled out of the bag.

Preferably, the garment of this second aspect of the invention is a garment according to the first aspect of the invention.

Another object of the invention is to provide a method for donning a compression garment.

This object is met by a method with the features of claim 13.

Other advantageous embodiments are listed in the dependent claims as well as in the description below.

BRIEF DESCRIPTION OF THE DRAWINGS

The above and other features and advantages of the present invention will become more apparent to those of ordinary skill in the art by describing in detail preferred embodiments thereof with reference to the attached drawings in which:

FIG. 5 illustrates an example embodiment of the disclosed compression garment according to the second aspect of the invention with six closing parts and six covers;

FIGS. 6a to 6d illustrate how the closing part is pulled out of a bag while wrapping the compression part and how a gauge indicates that a proper amount of compression force has been reached, and FIGS. 7a and 7b illustrate an alternative embodiment of the closing part.

MODES FOR CARRYING OUT THE INVENTION

Figure 1:
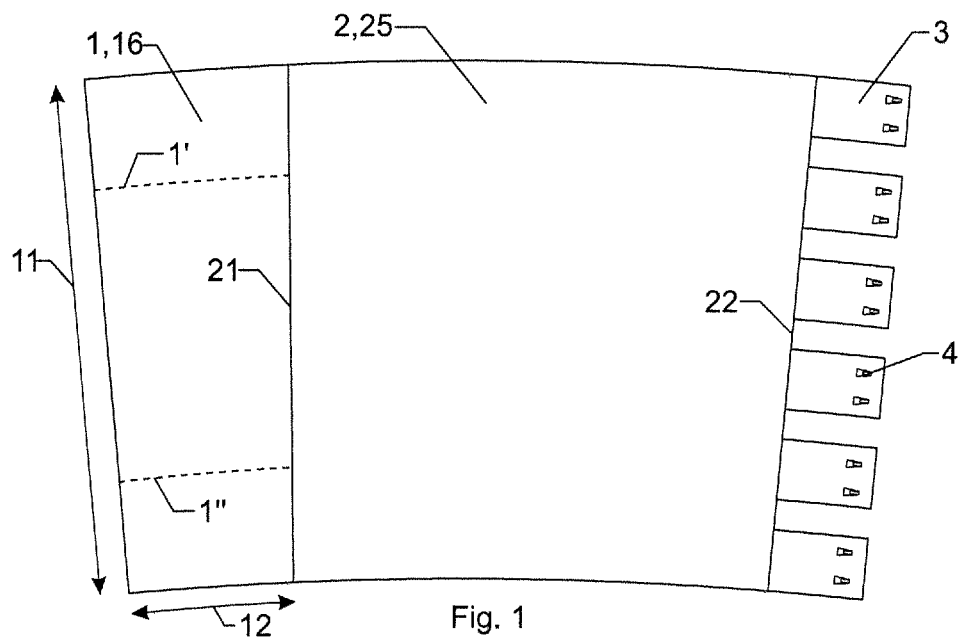
FIG. 1 illustrates an example embodiment of the disclosed compression garment according to the first aspect of the invention with an elongated stretchable sleeve, a compression part and six closing parts.

Advantageous embodiments of the invention are shown in FIGS. 1 to 7. FIG. 1 illustrates a compression garment which is adapted to be wrapped around a leg. The garment comprises an elongated stretchable sleeve 1 which is connected to a compression part 2. Furthermore, the compression garment comprises closing parts 3 connected to the compression part 2, in this example six closing parts 3, wherein each closing part 3 comprises at least one hook, in this example two hooks 4. The connection of the elongated stretchable sleeve 1 and the compression part 2 can be made of a stitched seam if both parts 1 and 2 are made of a fabric.

The compression part 2 has a first end 21 and a second end 22 wherein the second end 22 is located opposite to the first end 21. The first end 21 is located where the compression part 2 is connected to the elongated stretchable sleeve 1 and the second end 22 is located where the closing parts 3 are connected to the compression part 2. The closing parts 3 are made of a more stretchable material than the compression part 2 so that by stretching the closing parts and securing them to the compression part 2, preferably by hooks 4 or by other means, the compression part is held in its wrapped around state.

The compression part 2 extends over the full length 11 of the elongated stretchable sleeve 1 as shown in FIG. 1. In another embodiment, the compression part 2 may extend even further than the full length of the elongated stretchable sleeve at one of the opening sides of the stretchable sleeve 1 or the compression part 2 may extend further than the full length of the stretchable sleeve on both opening sides. This is indicated in FIG. 1 by a line 1' and a line 1" which shall indicate that the stretchable sleeve may end there, so that in this case its full length would be shorter than shown with arrow 11. A shorter stretchable sleeve will be easier to slip-through with the foot (see FIG. 4a) and as well be easier to place it on the lower leg (see FIG. 4b).

FIG. 1 shows a view directed to the spread out garment and to the outer surface 16 of the elongated stretchable sleeve and to the inner surface 25 of the compression part 2. If donned, the inner surface 25 of the compression part is in contact with the outer surface 16 of the elongated stretchable sleeve 1.

Figure 2:
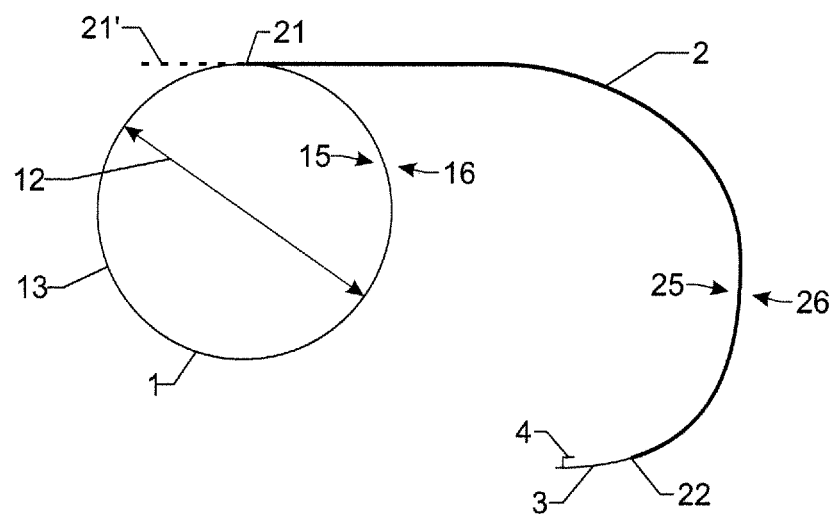
FIG. 2 illustrates an example embodiment with a view from above such that the unfolded shape of the elongated stretchable sleeve is visible.

FIG. 2 illustrates a compression garment with a view from above to the slip-in side of the elongated stretchable sleeve 1. The elongated stretchable sleeve 1 has a tubular form with a diameter 12 and a circumference 13 when being in an unfolded state as shown. If the compression garment is not donned, the circumference 13 of the elongated stretchable sleeve should optimally be somewhat smaller than the circumference of a body part, e.g. a leg, onto which the elongated stretchable sleeve 1 is pulled over.

The elongated stretchable sleeve 1 is made of a material which can be stretched with little effort so that only little strength is needed when donning it.

The compression part 2 is connected to the elongated stretchable sleeve 1 at its first end 21. At the second end 22 of the compression part, the closing parts 3 with hooks 4 are arranged. The compression part 2 is illustrated in FIG. 2 by a bold line.

The elongated stretchable sleeve 1 has an inner surface 15. When the garment is donned, the inner surface 15 of the elongated stretchable sleeve faces the skin of the body part, the outer surface 16 of the elongated stretchable sleeve 1 is in contact with the inner surface 25 of the compression part 2 and the outer surface 26 of the compression part 2 is the outermost surface of the compression garment.

The closing parts 3 with the hooks 4 are provided to be hooked into the outer surface 26 of the compression part 2.

The compression part 2 may extend with its end opposite the closing parts even a bit further than shown by the preferred embodiment of FIGS. 1 and 2. This is indicated in FIG. 2 by the dotted line showing a short section of the compression part extending over the convection line with the stretchable sleeve 1 and defining a free end 21'. In this case the reference 21 would only denote the connection line and not the end of the compression part which is denoted in this embodiment by 21'.

Figure 3:
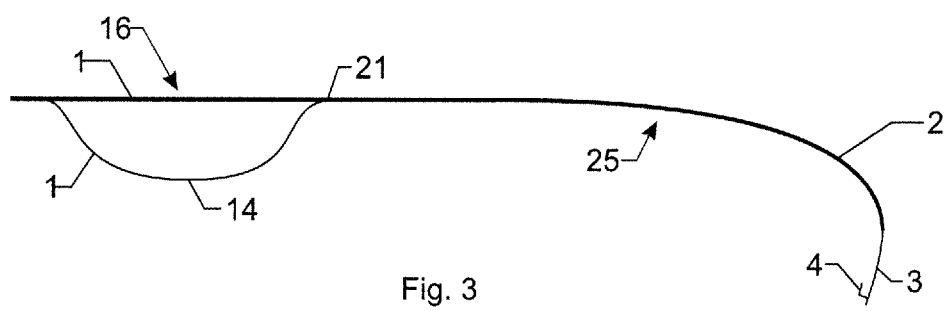
FIG. 3 illustrates an example embodiment with an alternative design of the elongated stretchable sleeve.

FIG. 3 illustrates an alternative design of a compression garment. In this embodiment, the elongated stretchable sleeve 1 is made of a textile part 14 which is attached on its one side to the first end 21 of the compression part 2, i.e. it is attached to the inner surface 25 of the compression part 2. On the other side it is attached to an extension of the compression part 2, which is therefore a part of the elongated stretchable sleeve 1.

This example shows that such terms as "elongated stretchable sleeve", "first end", "compression part" etc. have to be understood in a functional way. In other words it can be said that the stretchable sleeve may be attached at different locations on the inner surface 25.

FIGS. 4a to 4d illustrate a donning process, wherein the compression garment is donned over a lower leg.

In a first step (FIG. 4a), the elongated stretchable sleeve 1 is pulled over the lower leg by slipping-in foot first from one side into the tunnel-shaped elongated stretchable sleeve 1 and then pulling this sleeve over the lower leg. This step can be performed by only one hand. The elongated stretchable sleeve 1 is just brought into position on the lower leg in order to wrap the compression part 2 around the lower leg in further steps. By pulling the elongated stretchable sleeve 1 over the lower leg, the elongated stretchable sleeve 1 has to be stretched only with little effort.

As soon as the elongated stretchable sleeve 1 has been brought into position, it doesn't slide down since enough friction is provided between the elongated stretchable sleeve 1 and the lower leg because the elongated stretchable sleeve 1 is stretched by the lower leg.

In a second step (FIG. 4b and FIG. 4c), the compression part 2 and the closing parts 3 are wrapped around the lower leg. This step can be performed by only one hand since the compression part 2 is pulled from one side by the hand (from end 22) and the compression part 2 is held by the elongated stretchable sleeve 1 from the other side.

The more the compression part 2 is wrapped around the leg, the larger is the area 5 where the inner surface 25 of the compression part 2 touches the outer surface 16 of the elongated stretchable sleeve 1 and presses it to the lower leg. Hence, the compression garment is held even more stable in position and the compression part 2 can be pulled very strongly by one hand and the elongated stretchable sleeve 1 doesn't slip around the lower leg.

Figure 4A:
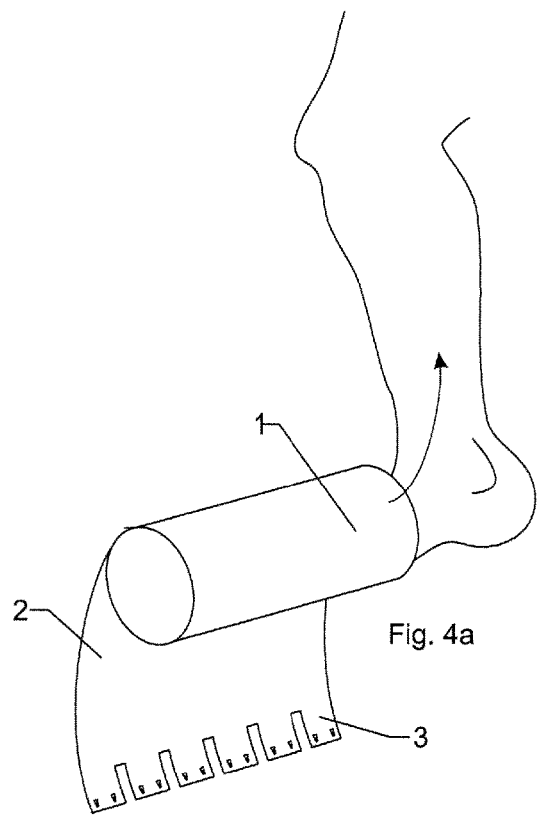
FIGS. 4a to 4d illustrate the donning process of the disclosed compression garment, wherein it is pulled over the leg, wrapped around the leg and fixed on the medial side of the leg.
Figure 4B:
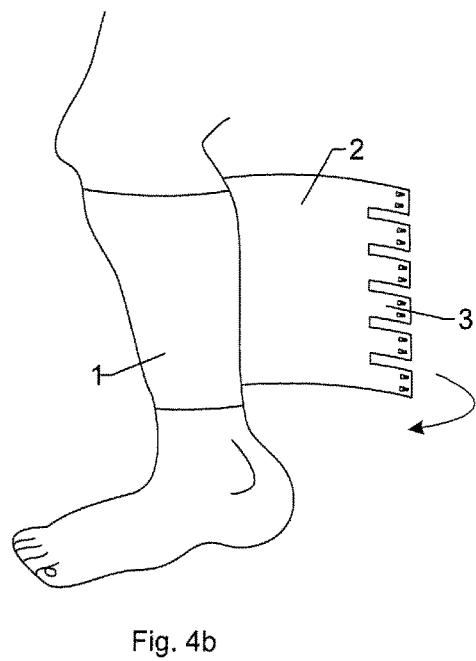
Figure 4C:
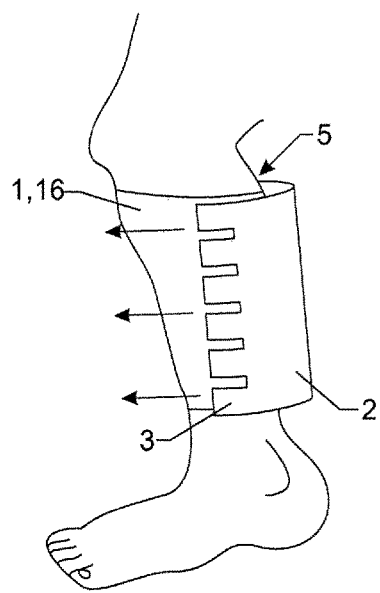
Figure 4D:
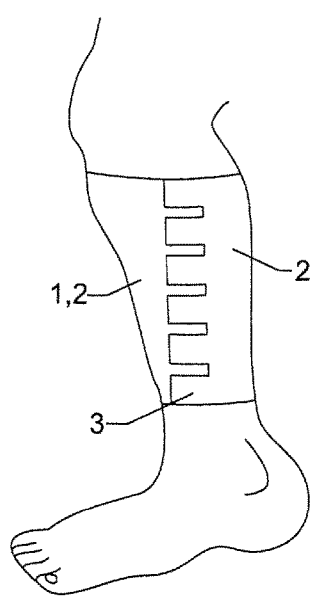

In a last step (FIG. 4d), the compression part 2 is attached in a stretched state by fixing the closing parts 3 to the compression part 2. Therefore, all steps for donning the compression garment can be performed by one hand which facilitates the donning process remarkably. FIG. 4d shows the closing on the medial side of the leg but of course the garment can be provided such that the wrapping around is done to the other side so that the closing parts of the garment are on the lateral side of the leg when the compression part has been wrapped around or any other position such as anterior or posterior aspects of the leg.

It is preferred that the elongated stretchable sleeve is shaped and sized such that the elongated stretchable sleeve alone applies an averaged pressure of less than approx. 15 mmHg (approx. 2000 Pa), in particular less than 10 mmHg (1333 Pa), in particular less than 5 mmHg (667 Pa), to the body part.

FIG. 5 illustrates an example embodiment for explaining the second aspect of the invention, this garment comprising a compression part 2, six closing parts 3 and six covers 6, such that every cover 6 partly covers one closing part 3. Preferably, this embodiment comprises as well an elongated stretchable sleeve 1. Otherwise only the compression part 2 would be present to be wrapped around the leg in a conventional manner. If there is an stretchable sleeve 1 all the features of the garment explained so far for the first aspect of the invention can be present.

The interaction of a closing part 3 and of a cover 6 is illustrated in detail by the FIGS. 6a to 6d and by the FIGS. 7a and 7b.

FIG. 6a shows a closing part 3 in an unstretched state with two hooks 4. No mark or gauge 71, 72, respectively, is visible because it is covered by the cover 6. The cover 6 is designed as a bag and the closing part 3 is secured within the bag in the region of the closed end of the bag and is in particular fixed inside the bag at that side 61 which is located opposite to the opening 62. The closing part 3 passes through the opening 62 such that one part of the closing part is covered by the cover 6 and the other part is not covered by the cover 6, i.e. one part is arranged inside and one part is arranged outside the bag.

As soon as the user pulls the closing part 3 in order to stretch the compression part 2, which is connected with the closing part 3, a bigger part of the closing part 3 gets visible because the surface of the closing part 3 increases since the closing part 3 is stretched in the direction indicated by the arrow in FIG. 6b.

If the closing part 3 and the compression part 2 are pulled further, a first mark or gauge 71, respectively, which is in this example designed as a simple line, appears, i.e. it moves out of the bag, and indicates that a proper amount of stretch in the compression part and/or in the closing part has been reached, as illustrated by FIG. 6c. In this moment, the user can fix the compression garment in a stretched state by attaching the closing part 3 to the elongated stretchable sleeve 1 or to the compression part 2.

It is also possible that a second mark or more marks or gauges 72, respectively, are applied to the closing part 3 such that different compression levels can be indicated by the first gauge 71 and the second gauge 72, as illustrated by FIG. 6d.

FIGS. 7a and 7b illustrate an alternative embodiment of the closing part 3 in an unstretched state (FIG. 7a) and in a stretched state (FIG. 7b). The cover 6 has a window 73 such that the at least one gauge 71, 72 is visible in the window 73 if not enough stretch has been reached and is covered by the cover 6 if enough stretch has been reached or is covered by the cover 6 if sufficient stretch has not been reached and is visible in the window 73 if sufficient stretch has been reached.

The present invention has so far been described for some specific embodiments shown in the figures. It must be noted that it also can be practiced differently.

The invention claimed is:

1. A compression garment for applying compression to a body part, the compression garment comprising:
   an elongated stretchable sleeve with an inner surface and an outer surface, wherein the elongated stretchable sleeve is adapted to be worn over the body part,
   a compression part connected to the elongated stretchable sleeve, and
   at least one closing part connected to the compression part for fixing the compression part in a stretched state,
   wherein the compression part is shaped and sized to be wrapped around at least a part of the circumference of the elongated stretchable sleeve and preferably to be wrapped around more than the full circumference of the elongated stretchable sleeve, to apply compression force to the body part,
   wherein the compression part extends at least over a full length of the elongated stretchable sleeve, wherein the compression part is a continuous part, wherein the compression part is adapted for positioning proximate to the outer surface of the elongated stretchable sleeve, and in that the compression part is fixable by the at least one closing part in the stretched state to maintain the compression force,
   wherein the compression part has a first end connected to the elongated stretchable sleeve and a second end located opposite to the first end, and wherein a plurality of closing parts are arranged adjacent to the second end.

2. A compression garment according to claim 1 wherein the compression part extends beyond the full length of the elongated stretchable sleeve on one end thereof or on both ends thereof.

3. A compression garment according to claim 1 wherein the closing part is provided by two or more strip-shaped elements each connected by one end to the compression part and each provided with at least one hook.

4. A compression garment according to claim 1, wherein the elongated stretchable sleeve is shaped and sized such that it alone applies an averaged pressure of less than 15 mmHg, in particular less than 10 mmHg, in particular less than 5 mmHg, to the body part.

5. A compression garment according to claim 1, wherein the elongated stretchable sleeve has a tubular form adapted to receive a leg or an arm.

6. A compression garment according to claim 1 wherein the elongated stretchable sleeve is integrally made of a material different than the material of the compression part or wherein the elongated stretchable sleeve is made in part of the material of the compression part and in part of a material different than the material of the compression part, in particular wherein the material of the stretchable sleeve is thinner and more stretchable than the material of the compression part.

7. A compression garment according to claim 1, wherein the compression part is made of spacer fabric.

8. A compression garment according to claim 1, wherein the compression part has an inner surface and an outer surface, wherein the at least one closing part and the outer surface of the compression part are adapted such that the at least one closing part is attachable to the outer surface of the compression part to fix the compression part in its stretched state.

9. A compression garment according to claim 1, wherein the compression garment are stockings or a bandage.

10. A method of donning a compression garment for applying compression to a body part, said garment comprising an elongated stretchable sleeve with an inner surface and an outer surface, wherein the elongated stretchable sleeve is adapted to be worn over the body part, a compression part connected to the elongated stretchable sleeve, and at least one closing part connected to said compression part for fixing the compression part in a wrapped around state, wherein the compression part is shaped and sized to be wrapped around at least a part of the circumference of the elongated stretchable sleeve, wherein the compression part is adapted for positioning proximate to the outer surface of the elongated stretchable sleeve, and wherein the compression part extends at least over a full length of the elongated stretchable sleeve, wherein the compression part is a continuous part, wherein the compression part has a first end connected to the elongated stretchable sleeve and a second end located opposite to the first end, and wherein a plurality of closing parts are arranged adjacent to the second end, wherein the method comprises:
   donning the elongated stretchable sleeve; and,
   wrapping the compression part around said body part for providing a compression force to the body part and the compression part is fixed by the at least one closing part in the wrapped around state to maintain the compression force.

* * * * *